(12) United States Patent
Huwiler et al.

(10) Patent No.: US 9,555,197 B2
(45) Date of Patent: Jan. 31, 2017

(54) BUBBLE TRAP SYSTEMS FOR INFUSION PUMP DEVICES

(71) Applicant: Roche Diagnostics International AG, Steinhausen (CH)

(72) Inventors: Christoph Huwiler, Baar (CH); Florian Kuhni, Wabern (CH); Andreas Geipel, Oftringen (CH)

(73) Assignee: Roche Diagnostics International AG, Rotkreuz (CH)

(*) Notice: Subject to any disclaimer, the term of this patent is extended or adjusted under 35 U.S.C. 154(b) by 246 days.

(21) Appl. No.: 14/274,128

(22) Filed: May 9, 2014

(65) Prior Publication Data
US 2014/0243782 A1    Aug. 28, 2014

Related U.S. Application Data

(63) Continuation of application No. 12/724,006, filed on Mar. 15, 2010, now Pat. No. 8,765,055.

(30) Foreign Application Priority Data

Mar. 16, 2009  (EP) .................... 09155216

(51) Int. Cl.
| A61M 37/00 | (2006.01) |
| A61M 5/36  | (2006.01) |
| A61M 5/38  | (2006.01) |
| A61J 1/10  | (2006.01) |
| A61M 5/14  | (2006.01) |

(52) U.S. Cl.
CPC . A61M 5/36 (2013.01); A61J 1/10 (2013.01); A61M 5/38 (2013.01); *A61M 5/141* (2013.01)

(58) Field of Classification Search
CPC .......... A61M 5/36; A61M 5/38; A61M 5/141; A61J 1/10
See application file for complete search history.

(56) References Cited

U.S. PATENT DOCUMENTS

| 3,007,334 | A |   | 11/1961 | Pall |
| 4,177,149 | A | * | 12/1979 | Rosenberg ......... B01D 19/0031 |
|           |   |   |         | 210/436 |
| 4,268,279 | A |   | 5/1981  | Shindo et al. |
| 4,395,260 | A |   | 7/1983  | Todd et al. |
|           |   |   |         | (Continued) |

OTHER PUBLICATIONS

International Search Report for application No. EP09155216, dated Aug. 7, 2009, 7 pages.

*Primary Examiner* — Leslie Deak
(74) *Attorney, Agent, or Firm* — Dinsmore & Shohl LLP

(57) ABSTRACT

Bubble traps for removing bubbles from a stream of liquid and flexible containers comprising such bubble traps are disclosed. The bubble trap includes a containment chamber fluidly coupled to an outlet conduit. At least one grate is disposed between the containment chamber and the outlet conduit. The at least one grate includes a plurality of grate inlets formed in a grate wall and fluidly coupled to the outlet conduit with a plurality of grate conduits such that the containment chamber is fluidly coupled to the outlet conduit. The grate traps bubbles entrained in the stream of liquid flowing from the containment chamber to the outlet conduit in the containment chamber when the bubbles are greater than or equal to a diameter of the grate inlets.

29 Claims, 6 Drawing Sheets

(56) References Cited

U.S. PATENT DOCUMENTS

| | | | |
|---|---|---|---|
| 4,493,705 A * | 1/1985 | Gordon | A61J 1/10 128/DIG. 3 |
| 4,983,102 A | 1/1991 | Swain | |
| 5,762,789 A | 6/1998 | De Los Reyes et al. | |
| 5,876,604 A | 3/1999 | Nemser et al. | |
| 5,951,870 A * | 9/1999 | Utterberg | A61M 1/3643 210/188 |
| 6,015,500 A | 1/2000 | Zuk, Jr. | |
| 6,168,648 B1 | 1/2001 | Ootani et al. | |
| 6,267,926 B1 | 7/2001 | Reed et al. | |
| 6,503,225 B1 | 1/2003 | Kirsch et al. | |
| 6,537,356 B1 | 3/2003 | Soriano | |
| 6,648,945 B1 | 11/2003 | Takeda et al. | |
| 7,097,690 B2 | 8/2006 | Usher et al. | |
| 7,654,414 B2 | 2/2010 | Hiranaga et al. | |
| 2007/0262076 A1 | 11/2007 | Johnson | |
| 2008/0087408 A1 | 4/2008 | Maezawa | |
| 2008/0180500 A1 | 7/2008 | Sugahara | |
| 2010/0292627 A1 * | 11/2010 | Caleffi | A61M 1/3627 604/5.01 |

* cited by examiner (a)

(b)

(a)

(b)

(c)

(d)

BUBBLE TRAP SYSTEMS FOR INFUSION PUMP DEVICES

CROSS REFERENCE TO RELATED APPLICATIONS

This application is a continuation of currently pending U.S. application Ser. No. 12/724,006 filed Mar. 15, 2010 which claims priority to European Patent Application No. EP09155216 filed Mar. 16, 2009 which is herein incorporated by reference in its entirety.

TECHNICAL FIELD

The embodiments described herein relate to bubble traps for removing bubbles from a stream of liquid, containers for storing a liquid medicament comprising such bubble traps, and devices for the automated release of liquid medicament incorporating such bubble traps and/or flexible containers.

BACKGROUND

Devices for the automated release of liquid medicaments are normally used with patients who have a continuous or variable need of a medicine that can be administered by subcutaneous infusion. Specific applications are, for example, certain pain therapies and the treatment of diabetes, in which computer controlled infusion pump devices, such as insulin pumps, are used. Such devices can be carried by a patient on the body and contain a certain amount of liquid medicament in a reservoir in the form of a container. The medicine reservoir often comprises medicine sufficient for one or more days. The liquid medicament is supplied to the patient's body from the reservoir through an infusion cannula or an injection needle.

In self-administration of medicaments, such as the self administration of insulin, the patients administering the medicament by means of an infusion pump device are increasingly emphasizing convenience and discretion. As a consequence, such infusion devices are designed to be as small as possible to increase discretion and improve patient comfort.

While there are fully or partially disposable single-use infusion pump devices, such devices are typically non-disposable and are loaded with a disposable drug cartridge. Such disposable cartridges are preferable for sterility and contamination prevention reasons. They may be delivered pre-filled with a certain liquid medicament, or empty, ready to be filled by a user.

One common type of infusion pump device that is carried on or near the body has a medicine reservoir with a cylindrical ampoule and a displacement piston, which is pushed into the ampoule by a piston rod or threaded spindle in order to convey the liquid medicament. These known designs have the disadvantage of being longer and/or thicker than desired.

In another type of infusion pump device the rigid container and movable piston of a syringe-type infusion pump are replaced by a flexible container. Such a container may, for example, have the form of two flexible wall sheets that are sealed together. The liquid medicament is obtained from the container by a downstream pump. Flexible containers have the advantage of a smaller volume surplus of the container in relation to its content, which reduces manufacturing costs and the achievable dimensions of an infusion pump device using such a flexible container. The volume of a flexible container for use in an infusion pump device may be up to 10 ml, but is preferably 5 ml or less, and more preferably lies in a range of 1.5 to 3.5 ml.

A known problem of infusion devices are air bubbles in the fluidic system, particularly in the pump system, but also in other components such as the container or a filling port. A certain volume of air present in the container cannot be avoided or completely removed. If said air remains in the container or in another part of the fluidic system, it may be administered in place of the liquid medicament, which leads to potentially dangerous dosing errors. Furthermore, the administration of air into a patient's body should be generally avoided for medical reasons.

Yet another problem of air in the fluidic system is the reduced stiffness of the fluidic system. Due to the high compressibility of gases such as air in relation to liquids such as water, it becomes difficult to measure the exact pressure in the fluidic system. This impedes the detection of blockages or occlusions in the fluidic system by measuring the fluidic pressure.

SUMMARY

According to one embodiment, a bubble trap for removing bubbles from a stream of liquid includes a containment chamber fluidly coupled to an outlet conduit. At least one grate is disposed between the containment chamber and the outlet conduit. The at least one grate includes a plurality of grate inlets formed in a grate wall and fluidly coupled to the outlet conduit with a plurality of grate conduits such that the containment chamber is fluidly coupled to the outlet conduit. The grate traps bubbles entrained in the stream of liquid flowing from the containment chamber to the outlet conduit in the containment chamber when the bubbles are greater than or equal to a diameter of the grate inlets.

In another embodiment, a flexible container for holding a fluid includes an outer wall of flexible material sealed with a peripheral sealing rim defining a containment chamber in the flexible material. An outlet conduit is fluidly coupled to the containment chamber. At least one grate is disposed between the containment chamber and the outlet conduit. The at least one grate comprises a plurality of grate inlets formed in a grate wall and fluidly coupled to the outlet conduit and the containment chamber with a plurality of grate conduits. Bubbles entrained in a stream of fluid flowing from the containment chamber to the outlet conduit are trapped in the containment chamber when the bubbles are greater than or equal to a diameter of the grate inlets.

It is to be understood that both the foregoing general description and the following detailed description describe various embodiments and are intended to provide an overview or framework for understanding the nature and character of the claimed subject matter. The accompanying drawings are included to provide a further understanding of the various embodiments, and are incorporated into and constitute a part of this specification. The drawings illustrate the various embodiments described herein, and together with the description serve to explain the principles and operations of the claimed subject matter.

DETAILED DESCRIPTION

Figure 1:
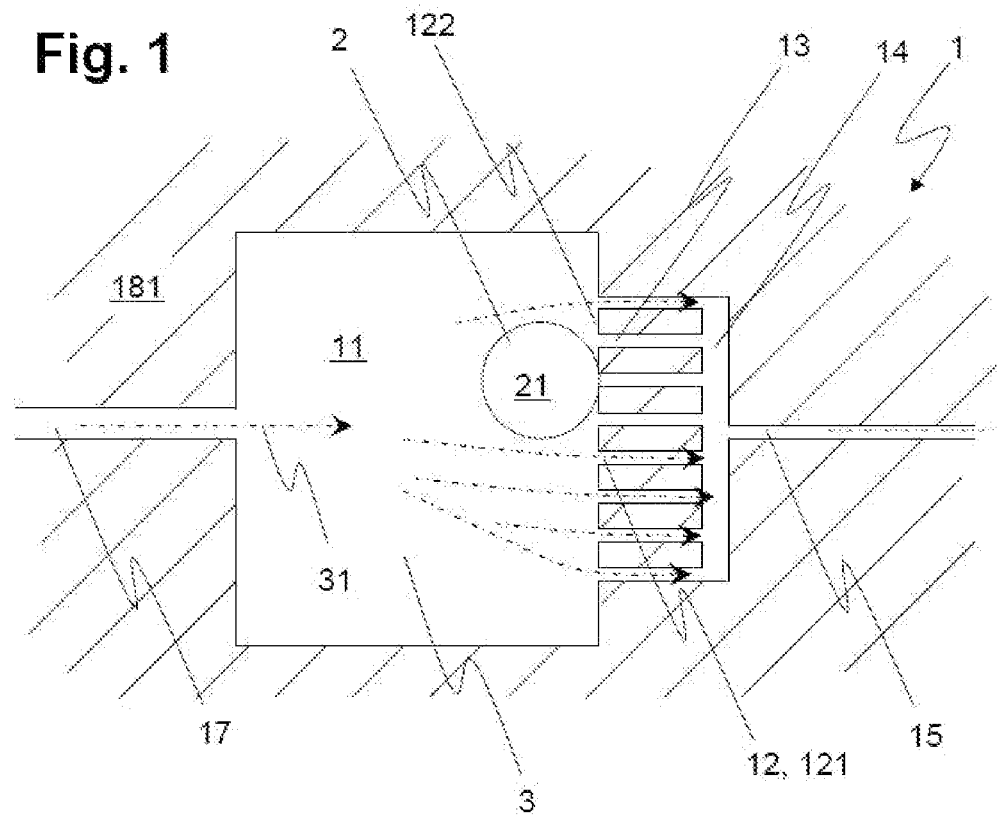
FIG. 1 schematically depicts a cross-section of a bubble trap according to one or more embodiments shown and described herein.

Bubble traps for removing bubbles from a stream of liquid, particularly in an infusion pump device or a container for storing a liquid medicament, are described herein. The bubble traps are able to retain bubbles exceeding a certain minimum size. The effectiveness of the bubble traps described herein is independent of the orientation of the bubble trap in three-dimensional space.

The bubble traps according to the embodiments described herein can be provided with high quality at low costs and comprise a minimum number of components. Flexible containers for storing liquid medicament incorporating bubble traps are also disclosed as well as devices for the automated release of liquid medicament which incorporate bubble traps, and/or flexible containers with bubble traps.

According to one embodiment, a bubble trap for removing bubbles from a stream of liquid includes a grate arranged in the stream which retains bubbles that are drifting in the stream. The grate comprises a grate wall and two or more grate inlets arranged on the grate wall with a certain, defined geometry, through which the stream can pass downstream. The shape of the grate inlets and/or the distribution of the grate inlets on the grate is designed such that a bubble larger than a certain minimum size cannot pass the grate without coming into contact with a grate inlet.

When a bubble arrives at a grate inlet of the bubble trap it will thus inevitably come into contact with the surface of the grate wall and the grate inlet. When the bubble enters the grate inlet, the contact area between grate and bubble will increase, and the contact area between bubble and liquid, as well as liquid and grate surface, will decrease. Due to the specific relations of the interface tensions between the gas mixture in the bubble, the grate surface and the liquid, such a state will have a higher potential energy compared to a state with the bubble not entering the grate inlet. Since the stream of liquid can pass through the other grate inlets of the grate, however, the necessary pressure difference across the grate will not increase to a value that is sufficient to force the bubble through the grate inlet. It thus will be retained in front of the grate inlet. The effect of the interface tension increases with decreasing dimensions of the grate inlets.

Thus, as an effect of the two or more grate inlets arranged on the grate wall, the liquid flow in the bubble trap cannot be blocked by one single bubble. In one embodiment, the shape and distribution of the arrangement of the two or more grate inlets on the grate wall are such that a bubble below a certain maximum size that is retained by the grate can block only a part of the combined cross-sectional area of the grate inlets.

In one embodiment of a bubble trap described herein, the material of the grate is selected such that the energy corresponding to the entry of a bubble in a grate inlet is as high as possible. This can be achieved by a grate material that is as hydrophilic as possible. Hydrophilicity of a surface correlates with the energy that has to be expended to separate water from the surface, and consequently with the interface tension between the aqueous liquid and the grate surface.

For the same reason, the shape of the at least one grate inlet is designed such that the relationship between the surface of the grate inlet and its cross-sectional area is as large as possible. This can be achieved by choosing the shape of a grate inlet such that the ratio between the circumference of the grate inlet (which is proportional to the inner surface of the grate inlet) and its cross-sectional area is larger than for a grate inlet with circular shape.

In one embodiment, the grate of the bubble trap, particularly the circumference of the grate inlets, is sharp-edged. This has the effect of causing a sudden increase in the potential energy of a bubble entering into a grate inlet due to the interface tension, while for soft, rounded or chamfered edges the increase would be less sudden. The latter would increase the probability of a bubble entering the grate inlet.

In one embodiment, a containment chamber may be arranged upstream of the grate. In another embodiment, the bubble trap may comprise two or more grates.

In yet another embodiment the bubble traps comprises 2 to 10 grate inlets which are arranged on the grate wall with a certain distance between each other.

In yet another embodiment, the bubble traps include, in order, from upstream to downstream: a supply conduit, a containment chamber, two or more separate grate conduits leading from a grate inlet to a common junction conduit, and an outlet conduit.

To increase the capacity and efficiency of the bubble traps described herein, a second containment chamber and a second grate may be arranged downstream of the first grate.

The bubble traps described herein may be embodied in a flexible container for storing a liquid medicament. In such an embodiment (which does not need additional parts or elements) the flexible container is formed from an outer wall comprising two wall sheets of flexible material that are sealed together with an insert part arranged between the two wall sheets with positive locking. The insert part comprises an essentially flat body with an inner conduit opening toward an upper surface of the body. The inner conduit is fluidly connected to two or more tubular conduits that lead to an outer edge of the body, and open to a containment chamber, or to a storage compartment of the flexible container.

In another embodiment of the bubble traps described herein, the bubble trap is embodied in a container for storing a liquid medicament comprising a port attached to an outer wall of the container. The port comprises a base plate having two or more tubular conduits that lead to an outer edge of the base plate. Said tubular conduits open to a special containment chamber or to a storage compartment of the flexible container.

In yet another embodiment described herein, the bubble trap is embodied in a flexible container for storing a liquid medicament with an outer wall consisting of two sheets of flexible material that are sealed together. Two or more drain channels are arranged between a storage volume and an access opening of the container. The two drain channels are formed by a cavity arranged on one or both of the two wall sheets, and open to a containment chamber, or to a storage compartment of the flexible container.

In another embodiment of the bubble traps described herein, a membrane is arranged in contact with a compartment directly upstream of the grate. The membrane is permeable to gases while retaining the liquid in the compartment. This allows bubbles retained in the bubble trap to leave the compartment thereby increasing the capacity of the bubble trap. An embodiment with such a degassing membrane is used with systems with overpressure, such as syringe type dosing pumps, since the pressure difference in the space behind the membrane will be the driving force for the air in the bubbles to pass through the membrane.

In another embodiment, a container for storing a liquid medicament includes a bubble trap as described herein, while a device for the automated release of a liquid medicament, particularly an infusion pump device, incorporates or is capable of using a bubble trap according to one or more embodiments described herein and/or a flexible container according to one or more embodiments described herein.

In a method for degassing a liquid, particularly a liquid medicament, a stream of liquid is directed through a bubble trap according to one or more embodiments of the bubble traps described herein. Prior to being put into operation the bubble traps are filled with liquid. Care is taken so that no bubbles are initially present in the bubble trap, particularly downstream of the grate. This can be achieved by filling the bubble trap upstream, supplying the liquid in reverse direction. Thus, in a method for filling a bubble trap an outlet conduit of the bubble trap is connected to a pressurized or non-pressurized liquid supply, such as a vial, and the bubble trap is filled with liquid in a reverse flow direction, from the outlet conduit through the grate inlets of the grate of the bubble trap. In one embodiment the bubble trap is evacuated prior to this reversed filling. The bubble trap may be connected upstream to a flexible container, which is also evacuated and subsequently filled with liquid, along with the bubble trap.

As used herein, the term "air" is meant to encompass any gas or mixture of gases forming stable bubbles in a liquid. The terms "medicament" and "liquid medicament" are meant to encompass any drug-containing flowable medicine, or therapeutic or diagnostic liquid, capable of being passed through a delivery element such as a hollow needle in a controlled manner, such as a liquid, solution, gel or fine suspension. Representative drugs include pharmaceuticals such as peptides, proteins, and hormones, biologically derived or active agents, hormonal and gene based agents, nutritional formulas and other substances in both solid (dispensed) or liquid form. In particular, the term medicament encompasses insulin preparations ready for administration. The terms "subcutaneous infusion" and "subcutaneous injection" are meant to encompass any method in which a needle device is inserted at a selected site within the body of a patient for subcutaneous, intravenous, intramuscular or intradermal delivery of a liquid medicament to a subject. Further, the term needle refers to a piercing member (including an array of micro needles) adapted to be introduced into or through the skin of a subject.

Referring now to the Figures, a cross-section of one embodiment of a bubble trap 1 is schematically shown in FIG. 1. A containment chamber 11 is in fluid communication with a reservoir of liquid and/or a conduit system delivering liquid. In the flow direction (from left to right in FIG. 1) a grate 12 for retaining bubbles in the stream of liquid 31 is arranged at the end of the containment chamber 11. In the embodiment depicted in FIG. 1 the grate 12 consists of a grate wall 122 on which six grate inlets 121 are arranged. The grate conduits 13 fluidly coupled to the six grate inlets 121 fluidly couple the grate inlets to a junction conduit 14 and an outlet conduit 15.

When a stream of liquid 31 comprising a bubble 21 flows in to the containment chamber 11, the bubble 21 moves toward a grate inlet 121 of the grate 12. However, due to the interface tensions between the air 2, the liquid 3, and the surface of the walls of the bubble trap 1, the pressure difference across the grate 12 necessary to force the bubble 21 through the grate inlet 121 and grate conduit 13 is larger than the pressure difference caused by the remaining grate inlets 121 that are not obstructed by the bubble 21. As a result, the bubble 21 does not enter the grate inlet 121, and remains in the containment chamber 11.

The grate inlets 121 are generally equal in size to or smaller than the bubbles 21 entrained in the stream of liquid 31. The minimum size of the bubbles that can be retained by a bubble trap 1 is defined by the maximum diameter of a spherical bubble that can enter a grate inlet 121 of the bubble trap 1. In one embodiment, the diameter of a grate inlet of the bubble trap is from about 0.01 to about 0.3 mm. In another embodiment, the diameter of the grate inlet is in a range from about 0.05 to about 0.2 mm.

In one embodiment, the edges of the grate inlets 121 are sharp instead of rounded or chamfered. Chamfered edges could reduce the retaining effect of the bubble trap as the potential energy due to the interface tension of a bubble entering the grate inlet increases more slowly.

The bubble trap 1 depicted in FIG. 1 will retain bubbles 21 as long as the total combined cross-sectional area of the remaining open grate inlets 121 is sufficient to keep the pressure difference across the grate 12 (i.e., the pressure difference between the containment chamber 11 and the outlet conduit 15), below the threshold where the bubble 21 could flow into the grate conduit 13. If only two grate inlets are present (i.e., a first grate inlet and a second grate inlet), the distance between the two grate inlets should, for example, be 5 to 100 times larger then the diameter of the grate inlet.

In one embodiment of a bubble trap the volume of the containment chamber 11 is sufficiently large to contain several bubbles and the area of the front of the grate 12 is sufficiently large to leave space for several bubbles. At the same time the volume of the containment chamber is as small as possible in order to keep the dead volume of a container or an infusion pump device in which the bubble trap is incorporated small. The dead volume is that part of liquid medicament volume that cannot be used because it cannot be removed from a container or an infusion pump device. For expensive liquid medicaments and/or small overall volumes of a container the dead volume can have a considerable detrimental effect on the cost efficiency. In one embodiment, the dead volume of a non-drainable containment chamber should be between about 20 to about 200 µl.

In an alternative embodiment, the grate 12 of the bubble trap may be arranged in a supply channel (instead of a containment chamber). The supply channel may be sufficiently wide to provide sufficient space for the retained bubbles.

Figure 2:
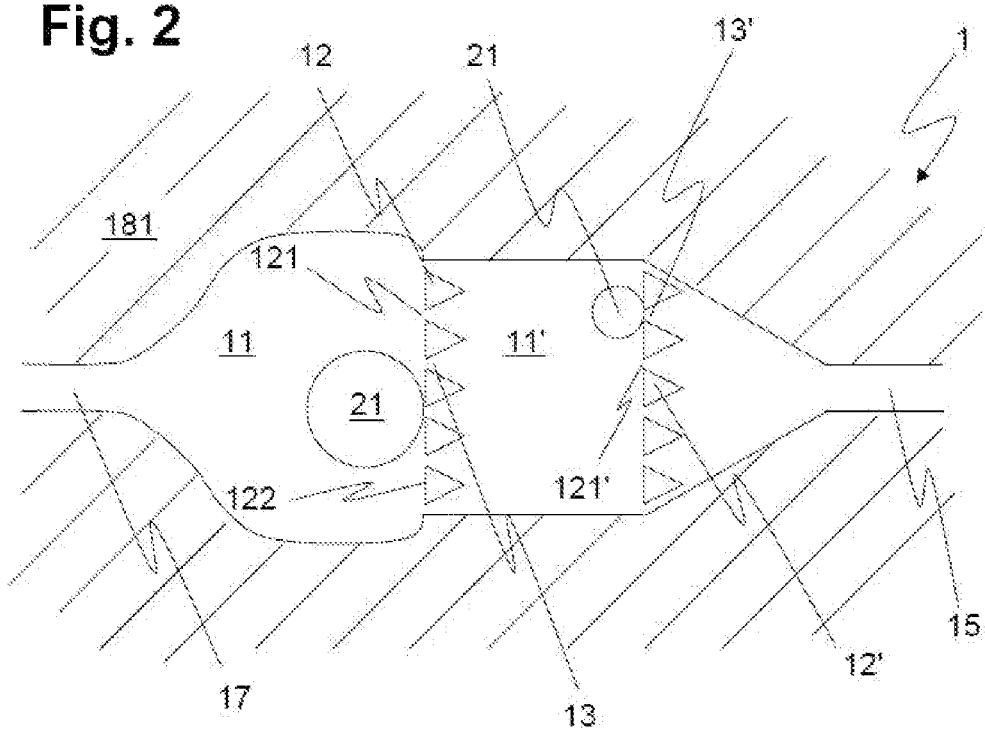
FIG. 2 schematically depicts a cross-section of a bubble trap with two containment chambers according to one or more embodiments shown and described herein.

FIG. 2 depicts another embodiment of a bubble trap 1 in which two containment chambers 11, 11' are arranged in series. A bubble 21 that passes through the first grate 12, arrives in a second containment chamber 11' where the bubble is retained. A bubble trap according to this embodiment may comprise more than two containment chambers and grates, which further increases the effectiveness and the capacity of the bubble trap and reduces the probability of a bubble to pass the bubble trap.

In the embodiment depicted in FIG. 2 the diameter of the grate conduits 13, 13' increases with increasing distance from the inlet conduit 17. This allows passage of a bubble 21 through the grate 12 in a downstream to upstream direction while preventing passage of a bubble 21 through the grate 12 in an upstream to downstream direction. When the bubble trap 1 is purposefully degassed by streaming liquid from downstream to upstream (right to left in FIG. 2), or when a container is filled via the bubble trap 1 (reverse filling), a bubble present in the downstream fluid system will easily pass through the grates 12, 12' in the reverse direction.

Figure 3:
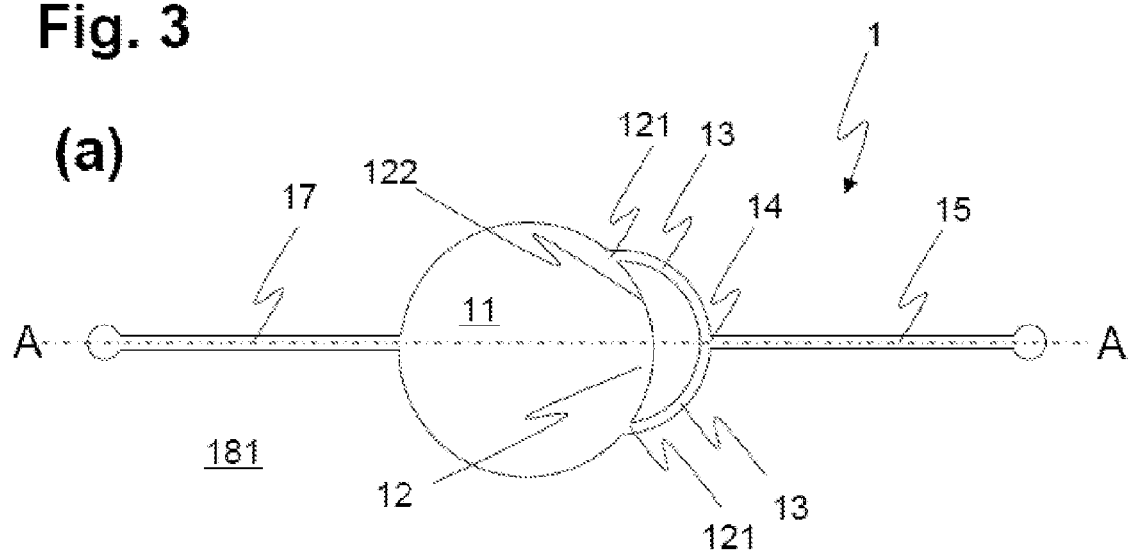
FIG. 3 schematically depicts a bubble trap according to one or more embodiments shown and described herein in (a) a top view with the cover removed, and (b) cross section.
Figure 3:
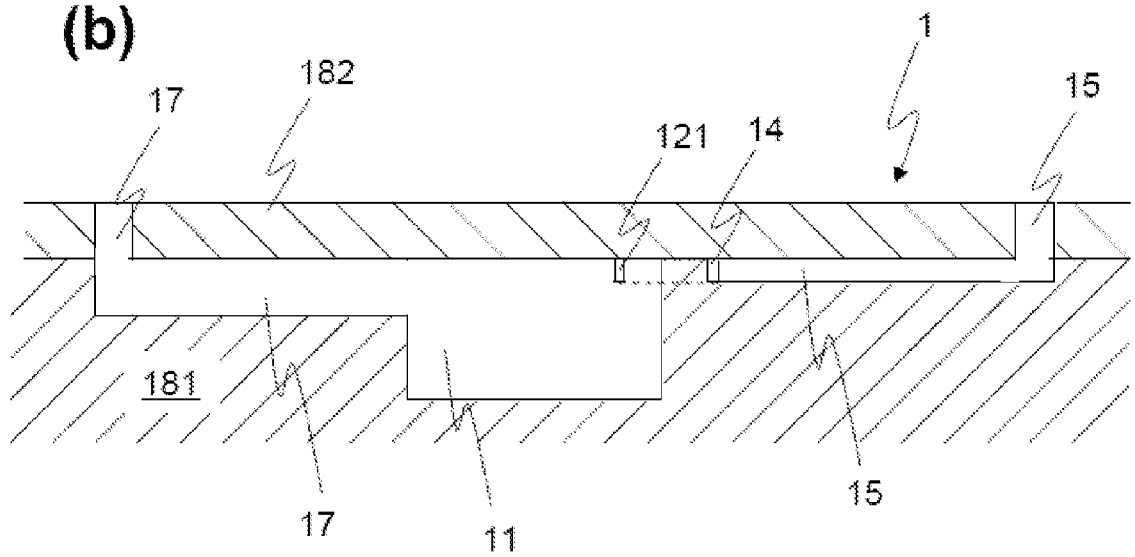

Yet another embodiment of a bubble trap is depicted in FIG. 3, (a) in a top view with cover 182 removed, and (b) in a cross-section along line A-A. The bubble trap 1 comprises a body 181 and a cover 182. A inlet conduit 17 is fluidly coupled to a cylindrical containment chamber 11. Two curved grate conduits 13 fluidly couple the containment chamber 11 to an outlet conduit 15 leading to a bubble trap outlet.

The height of the containment chamber 11 is greater than the height of the grate inlets 121 to provide sufficient space for retained bubbles and to decrease the cross-sectional area of the grate inlets 121 in relation to the total area of the grate wall 122 thereby improving the trap effect. Another advantage of this embodiment is that the grate inlets 121 are offset with respect to the supply/inlet conduits 17.

In one embodiment of the bubble trap, the walls of the conduits 17, 13, 15 and the containment chamber 11 are slightly sloped, which allows the use of a simple injection-molding tool for the manufacture of the bubble trap.

Figure 4:
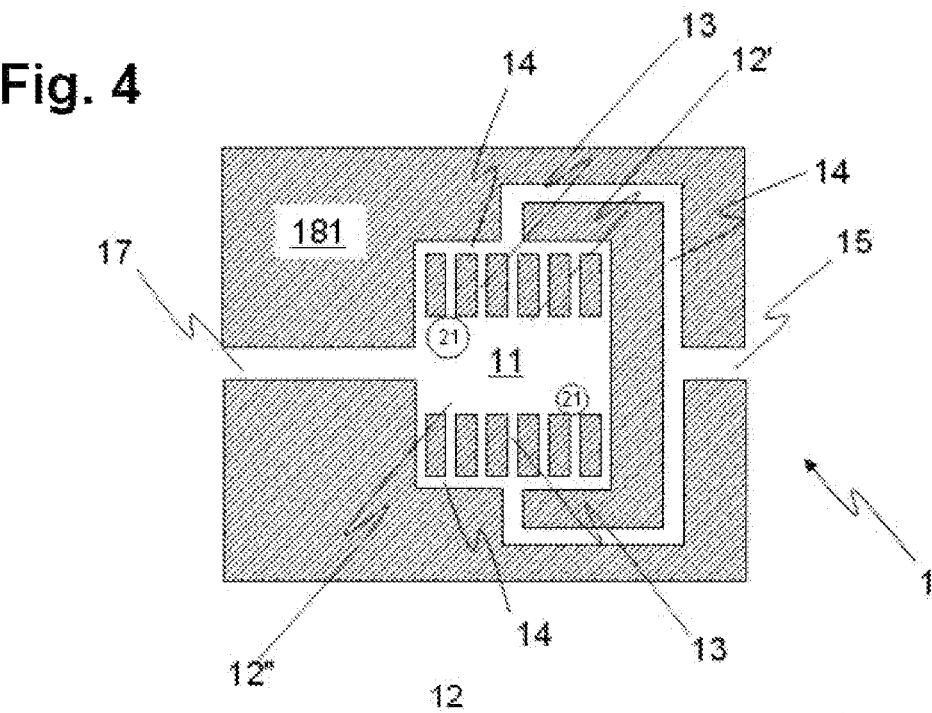
FIG. 4 schematically depicts a cross-section of a bubble trap with two grates according to one or more embodiments shown and described herein.

FIG. 4 depicts another possible embodiment of a bubble trap 1. In this embodiment, the bubble trap 1 includes two grates 12', 12" arranged in parallel on opposite sides of the containment chamber 11. The grate conduits 13 of both grates 12', 12" intersect at a common junction conduit 14 fluidly coupled to an outlet conduit 15. The two sub-grates 12', 12" are thus part of one common grate of the bubble trap 1. Depending on the orientation of the bubble trap in space, the bubbles 21 may remain on the sub-grate lying on the upper side, while the other sub-grate remains free of bubbles. In an alternative embodiment the bubble trap 1 may include three or more sub-grates. In particular, the containment chamber 11 may comprise a multitude of walls that are all equipped with a sub-grate 12', 12".

The embodiments of bubble traps depicted in FIGS. 1-4 may be integrated into an adapter or connection device located between a container or reservoir of liquid medicine and a pump device.

Alternatively, it may be possible to integrate the bubble trap 1 in certain parts or elements of an infusion pump device and/or a flexible container for a liquid medicament. In the European patent application entitled "Flexible container with insert part" filed on the same day as the parent of the present application, an advantageous flexible container for storing a liquid medicament is disclosed. Said application is hereby incorporated by reference as part of this disclosure in its entirety.

The flexible container disclosed in said application comprises an outer wall consisting of two wall sheets of flexible material that are sealed together, a storage compartment for the liquid medicament, and an access point on one of the wall sheets. The storage compartment and the access point are fluidly coupled. The access point is adapted to be fluidly coupled to an outer conduit system, such as an infusion pump device. An insert part is arranged between the two wall sheets with positive locking for fluidly connecting the storage compartment and the access point.

Figure 5:
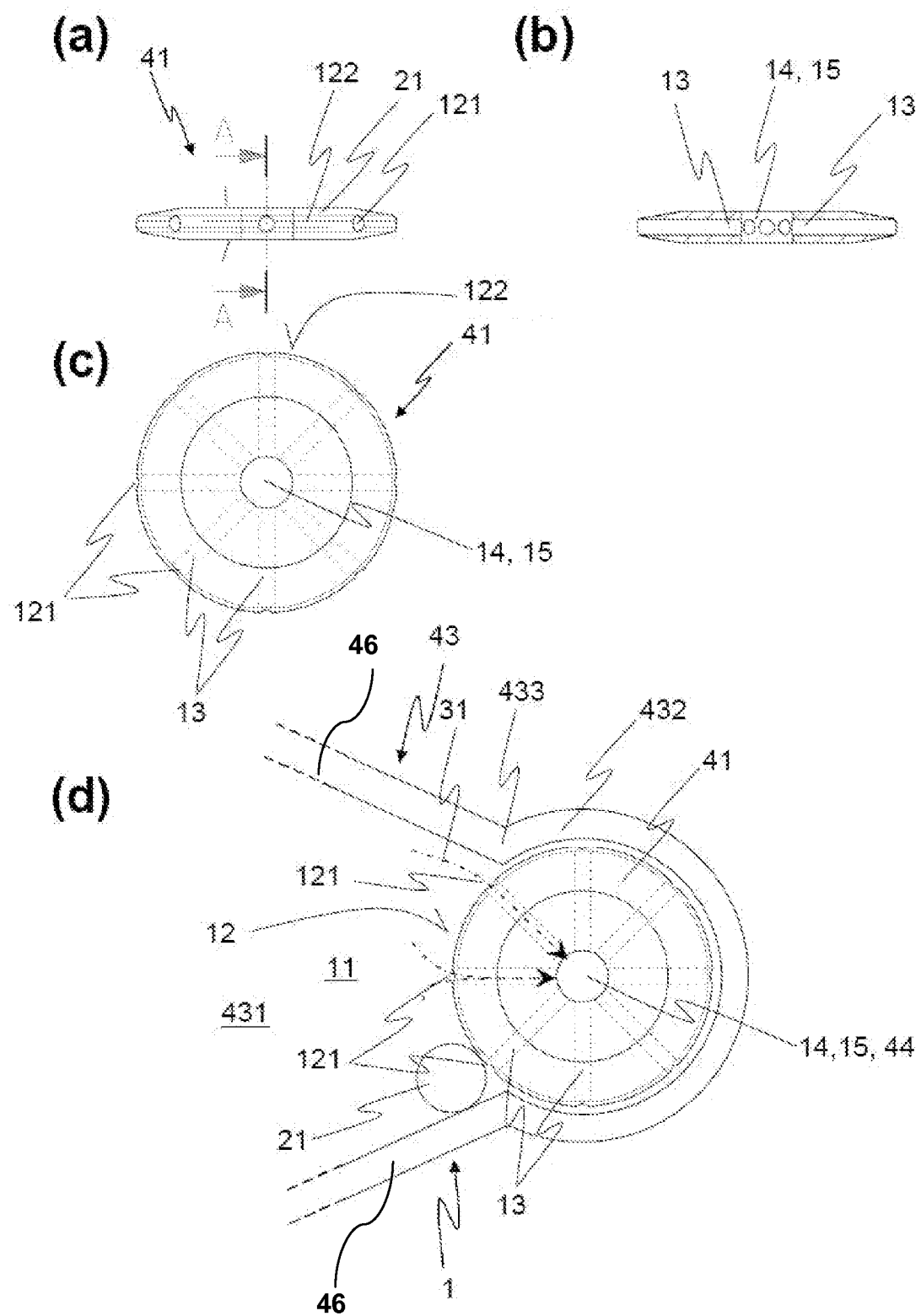
FIG. 5 schematically depicts a variant of a bubble trap according to one or more embodiments shown and described herein incorporated in a flexible container with an insert part shown in (a) side view, (b) cross-section, and (c) top view, and (d) the flexible container with the insert part.

FIGS. 5(a) to 5(c) depict an embodiment of an insert part 41, and a detail of a flexible container 43 with such an insert part 41 is shown in FIG. 5(d). The flexible container 43 and the insert part 41 function together as a bubble trap 1. On one end of the flexible container the insert part 41 is arranged between the two wall sheets 46 of the container 43. The sealing rim 432 forms a neck 433 that is smaller than the diameter of the disc shaped insert part 41, thereby positively locking the insert part within the flexible container.

The insert part 41 of the flexible container has an essentially disc-shaped form, with an outlet conduit 15 arranged in the center of the disc which leads to an access point 44 in the outer wall of the container. Eight tubular grate conduits 13 are radially arranged inside the body 181 of the insert part 41. Due to the highly symmetric form of the insert part, the angular orientation of the insert part in relation to the flexible container is irrelevant. In every orientation angle at least one grate conduit 13 will open to the storage compartment (i.e., the containment chamber 11) of the container, providing a fluid connection between the access point 44 and the containment chamber. It should be understood that the containment chamber 11 shown in the embodiments of the flexible containers depicted in FIGS. 5-7 acts as both a containment chamber for trapped bubbles as well as storage compartment 431 for liquids such as liquid medicaments. Accordingly, for purposes of describing the flexible containers of FIGS. 5-7, the phrases "containment chamber" and "storage compartment" may be used interchangeably.

The container 43 and the insert part 41 form a bubble trap 1. The openings of the grate conduits 13 that face toward the inner storage compartment 431 act as the grate inlets 121 of the grate 12 of the bubble trap 1. A bubble 21 arriving at the insert part 41 cannot enter a grate conduit 13, and thus will be retained inside the storage compartment 431 of the container 43.

Figure 6:
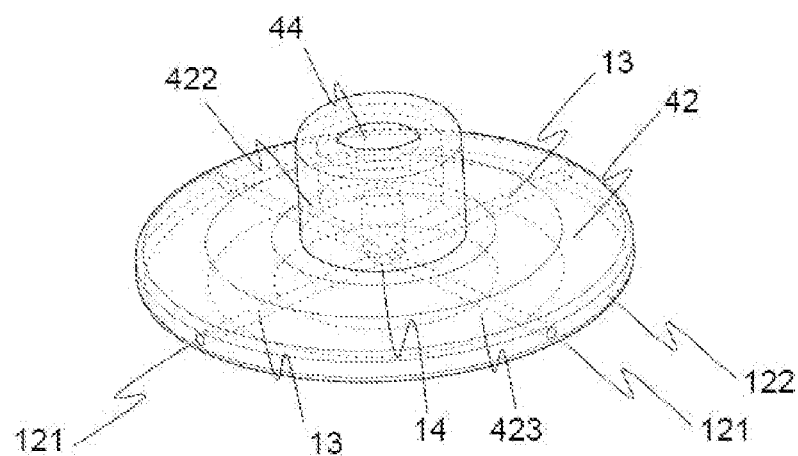
FIG. 6 schematically depicts another variant of a bubble trap according to one or more embodiments shown and described herein embodied in a flexible container with a port shown in (a) perspective view, (b) top view, and (c) cross-sectional view, and (d) with the port mounted on the flexible container.
Figure 6:
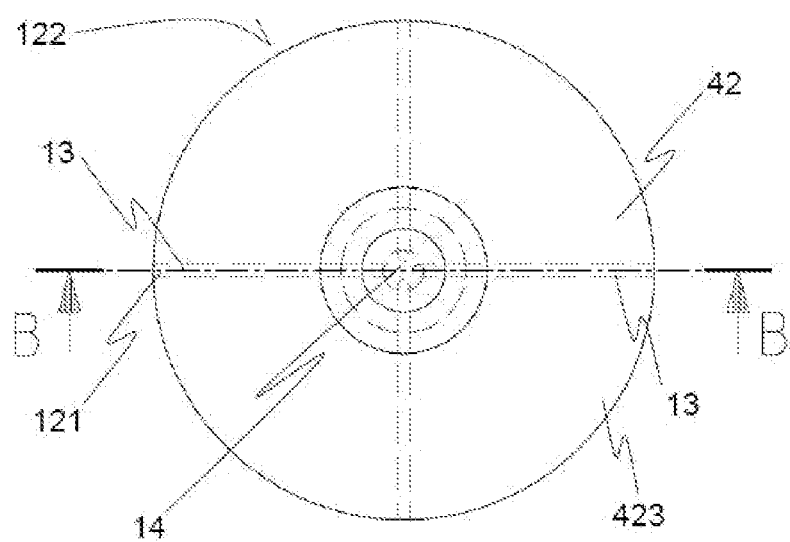
Figure 6:
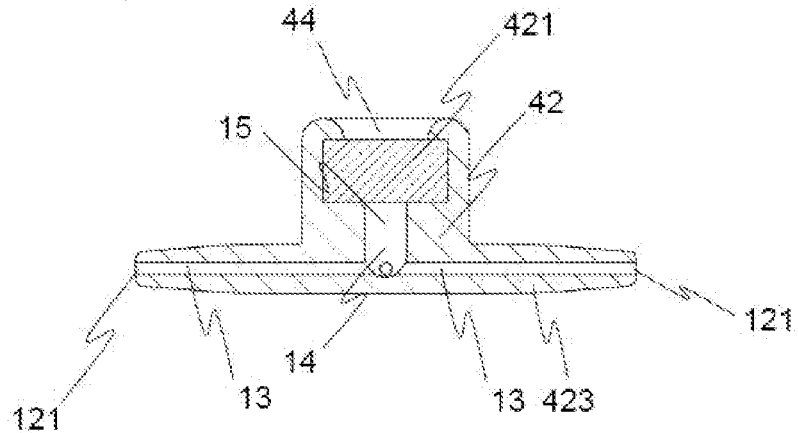
Figure 6:
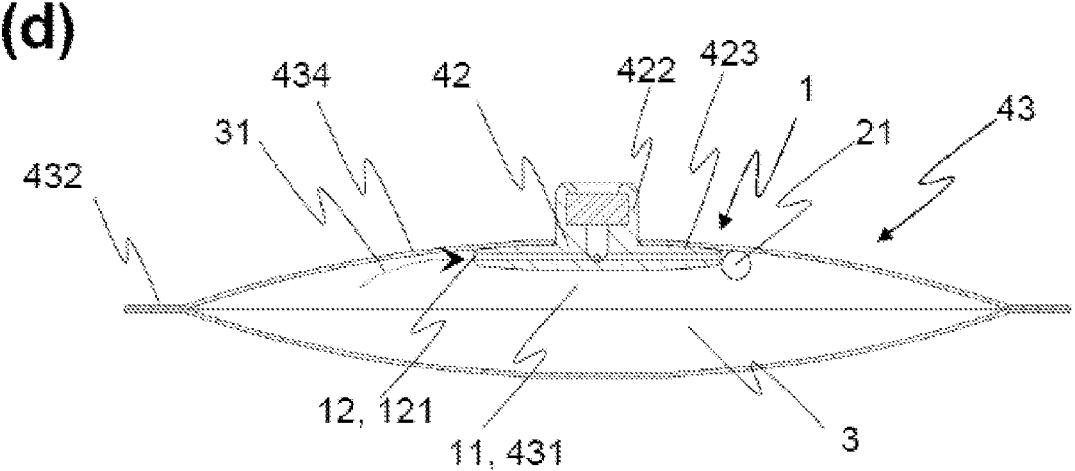

FIG. 6 depicts another embodiment of a bubble trap 1 formed in a flexible container. Flexible containers may be provided with one or more ports mounted to the container wall, in addition to the access area. These ports may be used for transferring liquid to and from the storage compartment of the container, or may be used to de-aerate the container. A particularly advantageous form of such a port is disclosed in European Patent Application No. 08167548 of the applicants, which is hereby incorporated by reference as part of this disclosure in its entirety. Said application teaches a flexible container for storing a liquid medicament comprising two walls consisting of a flexible, sheet-like material, and a port mounted to the wall for transferring liquid to and from a storage compartment of the container. The port has a flange that is sealingly attached to the wall, and an inner conduit connecting the storage compartment and the exterior of the container. The port comprises a base plate facing the storage compartment with at least one drain channel arranged on said base plate. The drain channels are connected to the inner conduit via an inner opening located on the base plate.

The ports disclosed in European Application No. 08167548 can be modified to act as bubble traps 1 without affecting the other advantageous effects of the ports. An example of such a modified port 42 is depicted in FIG. 6. The port 42 shown in FIGS. 6(*a*) to 6(*c*) comprises an adapter 422 arranged on a base plate 423. When mounted on a flexible container 43 (FIG. 6(*d*)), the adapter 422 protrudes through a circular hole in the container wall 434. The surface of the base plate 423 on the same side as the adapter forms the flange for mounting the port 42 to the wall 434. Said flange is sealed to the inner side of the wall by ultrasonic welding or gluing forming a liquid tight seal therebetween.

Four tubular grate conduits 13 are arranged in the base plate 423, leading from the peripheral edge (i.e., the grate wall 122) of the base plate to a central junction conduit 14 in fluid communication with an outlet conduit 15. The outlet conduit 15 terminates in the base plate at the junction conduit 14. In the embodiment depicted, a septum 421 made from, for example, silicon polymer, is arranged in the outlet conduit 15. This embodiment is suitable for use in conjunction with a hollow needle which may be used to penetrate the septum 421 to connect the containment chamber 11 of the container 43 to an outer conduit system, and to transfer liquid medicament into and out of the flexible container 43.

When mounted on a flexible container 43, as shown in FIG. 6(*d*), the port 42 in combination with the container 43 forms a bubble trap 1. The four openings of the grate conduits 13 facing the inner storage compartment 431 act as the grate inlets 121 of the grate 12 of the bubble trap 1. As described above, the containment chamber 11 of the bubble trap is the storage compartment 431. A bubble 21 in the container arriving at the port 42 cannot enter the grate conduits 13, and thus will be retained inside the storage compartment 431 of the container 43.

Figure 7:
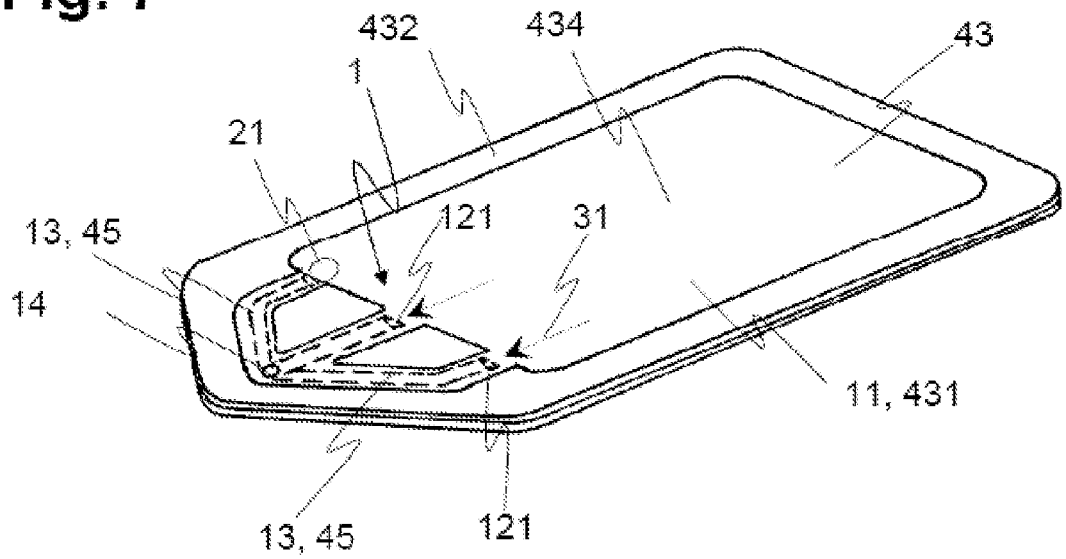
FIG. 7 schematically depicts a bubble trap as an integral part of a flexible container according to one or more embodiments shown and described herein.

FIG. 7 depicts yet another embodiment of a bubble trap 1 embodied in a flexible container. The flexible container is a modification of a flexible container for storing a liquid medicament disclosed in applicant's European Patent Application No. 08170627. The content of said application is hereby incorporated by reference as part of this disclosure in its entirety. These flexible containers comprise a wall consisting of two sheets of flexible material that are sealed together, a storage compartment for liquid medicament, and an access opening fluidly coupled to the storage compartment intended to be fluidly connected to an external conduit, for example of an infusion pump device. A drain channel is arranged between the storage compartment and the access opening, the drain channel formed by a cavity on one or both of the wall sheets. In one embodiment, the cavity may be located between an oblong corrugation or groove in one of the wall sheets and the opposite sheet.

Such a flexible container as described above can be modified to include a bubble trap. An example of such a flexible container with a bubble trap 1 is shown in FIG. 7. The flexible container 43 comprises two wall sheets 434 that are sealed along a peripheral sealing rim 432, and form a storage compartment 431. On one end of the container three drain channels 45 are arranged in a broadened area of the sealing rim 432, formed by oblong depressions in one of the wall sheets. It should be understood that the drain channels 45 in the embodiment of the flexible container shown in FIG. 7 also act as grate conduits 13 and, as such, the phrases "drain channel" and "grate conduit" may be used interchangeably when describing the flexible container depicted in FIG. 7. The drain channels 45 are fluidly coupled at a common junction conduit 14, and lead to the storage compartment 431. In contrast to the flexible containers disclosed in European Patent Application No. 08170627 of the applicants, where only one drain channel fluidly couples the access opening and the storage compartment, the multitude of narrow drain channels 45 opening to the storage compartment 431 act as a grate 12 of a bubble trap 1. When a bubble arrives at a grate inlet 121 of one of the grate conduits 13 of the bubble trap, it will be retained and remains in the containment chamber 11 (i.e., storage compartment 431).

In the embodiments of the bubble traps described thus far the grate inlets 121 are circular or elliptical shape. However, since the mechanism of the bubble trap is based on the fact that there is considerably higher interface tension between the air of the bubble and the surface of the bubble trap body than between the liquid and the surface of the bubble trap, and the energy related to the interface tension is proportional to the interface area, the potential interface area between an entering bubble 21 and the grate inlet 121 and grate conduit 13 should be as large as possible in order to increase the bubble trap effect. Thus, the shape of the grate inlet and/or the grate conduit may be any suitable shape that increases the interface area.

Figure 8:
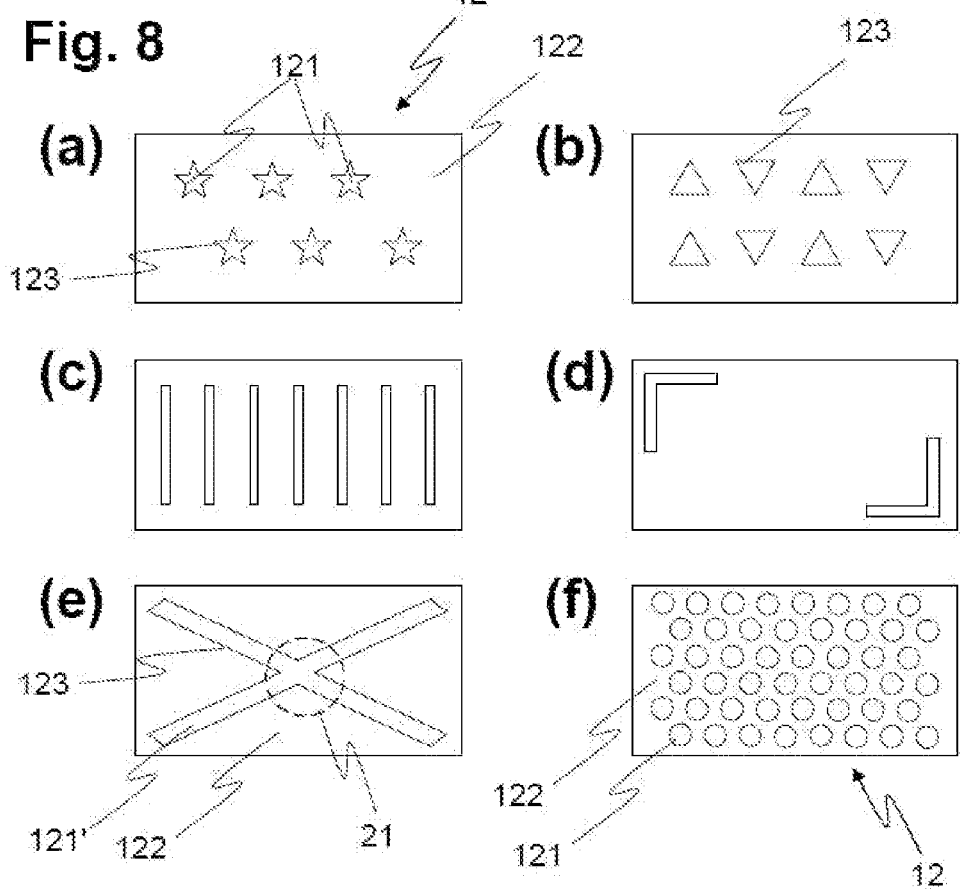
FIG. 8 schematically depicts different variants of grate inlets for a bubble trap according to one or more embodiments shown and described herein.

FIG. 8 schematically depicts different variants of grate inlets 121 of a bubble trap and their distribution on the grate 12. For example the grate inlets may have a star-like shape as in FIG. 8(*a*), or a triangular shape, as in FIG. 8(*b*). These two variants have the advantage that the surface of the bubble trap body that will be in contact with the air of a bubble of a given volume will be larger than for an grate inlet having a circular shape with the same cross-sectional area. Accordingly, it should be understood that a ratio of a circumference 123 of the grate inlet in these embodiments to the cross-sectional area of the grate inlet is greater than a ratio of the circumference to the cross-sectional area of a circular grate inlet with the equivalent cross-sectional area. FIG. 8(*c*) depicts an embodiment with grate inlets in the form of parallel slots, and FIG. 8(*d*) depicts an embodiment with two chevron-like grate inlets 121.

FIG. 8(*e*) depicts an embodiment of a bubble trap in which only one single cross-like shaped grate inlet 121 is arranged. Although this embodiment actually comprises only one grate inlet 121 and one grate conduit 13, and the overall cross-sectional area of the grate inlet 121 may be even larger than the cross-section of the bubble 21 to be retained (symbolized by the dashed circle), the local cross-sectional area of the grate inlet across the dimensions of a bubble will be smaller, and consequently the bubble is retained. The one single grate inlet 121' thus, in effect, acts as a multitude of discrete grate inlets 121 and, consequently, should be understood as "two or more grate inlets 121." FIG. 8(*d*) depicts a further variant, in which the density of grate inlets 121 is higher than in the previously discussed examples. The resulting grate 12 is essentially a sieve.

One particular advantage of the embodiments of the bubble traps shown in FIG. 8(*f*) is that the grate inlets 121 are arranged on the grate 12 in a way that ensures that, for every conceivable orientation of a bubble, there is at least one grate inlet 121 that is not blocked by the bubble 21. Of course, theoretically all grate inlets may be blocked by a multitude of bubbles. However, depending on the current orientation of the bubble trap in three-dimensional space, the retained bubbles may tend to move upwards, leaving the grate inlets located downwards free. Furthermore, due to interface tension, neighboring bubbles tend to coalesce, forming one single bubble that blocks a smaller area of the grate.

It will be apparent to those skilled in the art that various modifications and variations can be made to the embodiments described herein without departing from the spirit and scope of the claimed subject matter. Thus it is intended that the specification cover the modifications and variations of the various embodiments described herein provided such modification and variations come within the scope of the appended claims and their equivalents.

What is claimed is:

1. A method for degassing a liquid comprising:
   providing a bubble trap comprising
      a containment chamber;
      an outlet conduit; and
      at least one grate disposed between the containment chamber and the outlet conduit, the at least one grate comprising a plurality of grate inlets formed in a grate wall fluidly coupled to the outlet conduit with a plurality of grate conduits such that the containment chamber is fluidly coupled to the outlet conduit wherein the grate traps bubbles entrained in the stream of liquid flowing from the containment chamber to the outlet conduit in the containment chamber when the bubbles are greater than or equal to a diameter of a grate inlet, wherein the diameter ranges from 0.05 mm to 0.2 mm;
   connecting the bubble trap to a pressurized liquid supply;
   evacuating the bubble trap;
   filling the bubble trap with liquid in a reverse flow direction, from the outlet conduit through the grate inlets of the grate of the bubble trap to remove bubbles from the bubble trap prior to operation of the bubble trap;
   directing a stream of liquid through the bubble trap to degas the liquid; and
   passing a peptide, protein, hormone, insulin or a solid in the liquid through the bubble trap.

2. The method of claim 1 further comprising evacuating a flexible container connected to the bubble trap, wherein the bubble trap is connected upstream to the flexible container.

3. The method of claim 2 further comprising filling the flexible container with the liquid.

4. The method of claim 2 further comprising storing a medicament in the flexible container.

5. The method of claim 2 further comprising automatically releasing the medicament via an infusion pump coupled to the flexible container.

6. The method of claim 1 wherein the directing the stream of liquid through the bubble trap comprises directing the liquid through grate inlets each having a star-like shape or a triangular shape.

7. The method of claim 1 wherein the directing the stream of liquid through the bubble trap comprises directing the liquid through grate inlets each having chevron-like grate inlets.

8. The method of claim 1 further comprising evacuating the bubble trap prior to the filling.

9. The method of claim 1 wherein a peptide is passed in the liquid through the bubble trap.

10. The method of claim 1 wherein a hormone is passed in the liquid through the bubble trap.

11. The method of claim 1 wherein insulin is passed in the liquid through the bubble trap.

12. The method of claim 1 wherein a solid is passed in the liquid through the bubble trap.

13. The method of claim 1 wherein a protein is passed in the liquid through the bubble trap.

14. A method for degassing a liquid comprising:
    providing a bubble trap comprising
       a containment chamber;
       an outlet conduit; and
       at least one grate disposed between the containment chamber and the outlet conduit, the at least one grate comprising a plurality of grate inlets formed in a grate wall fluidly coupled to the outlet conduit with a plurality of grate conduits such that the containment chamber is fluidly coupled to the outlet conduit wherein the grate traps bubbles entrained in the stream of liquid flowing from the containment chamber to the outlet conduit in the containment chamber when the bubbles are greater than or equal to a diameter of a grate inlet;
    connecting the bubble trap to a non-pressurized liquid supply;
    filling the bubble trap with liquid in a reverse flow direction, from the outlet conduit through the grate inlets of the grate of the bubble trap to remove bubbles from the bubble trap prior to operation of the bubble trap;
    directing a stream of liquid through the bubble trap to degas the liquid; and
    passing a peptide or protein in the liquid through the bubble trap.

15. A method for degassing a liquid comprising:
    providing a bubble trap comprising
       a containment chamber;
       an outlet conduit; and
       at least one grate disposed between the containment chamber and the outlet conduit, the at least one grate comprising a plurality of grate inlets formed in a grate wall fluidly coupled to the outlet conduit with a plurality of grate conduits such that the containment chamber is fluidly coupled to the outlet conduit wherein the grate traps bubbles entrained in the stream of liquid flowing from the containment chamber to the outlet conduit in the containment chamber when the bubbles are greater than or equal to a diameter of a grate inlet;
    connecting the bubble trap to a non-pressurized liquid supply;
    filling the bubble trap with liquid in a reverse flow direction, from the outlet conduit through the grate inlets of the grate of the bubble trap to remove bubbles from the bubble trap prior to operation of the bubble trap;
    directing a stream of liquid through the bubble trap to degas the liquid; and
    passing a hormone in the liquid through the bubble trap.

16. A method for degassing a liquid comprising:
    providing a bubble trap comprising
       a containment chamber;
       an outlet conduit; and
       at least one grate disposed between the containment chamber and the outlet conduit, the at least one grate comprising a plurality of grate inlets formed in a grate wall fluidly coupled to the outlet conduit with a plurality of grate conduits such that the containment chamber is fluidly coupled to the outlet conduit wherein the grate traps bubbles entrained in the stream of liquid flowing from the containment chamber to the outlet conduit in the containment chamber when the bubbles are greater than or equal to a diameter of a grate inlet;

connecting the bubble trap to a non-pressurized liquid supply;

filling the bubble trap with liquid in a reverse flow direction, from the outlet conduit through the grate inlets of the grate of the bubble trap to remove bubbles from the bubble trap prior to operation of the bubble trap;

directing a stream of liquid through the bubble trap to degas the liquid; and passing insulin through the bubble trap.

17. A method for degassing a liquid comprising:
providing a bubble trap comprising
a containment chamber;
an outlet conduit; and
at least one grate disposed between the containment chamber and the outlet conduit, the at least one grate comprising a plurality of grate inlets formed in a grate wall fluidly coupled to the outlet conduit with a plurality of grate conduits such that the containment chamber is fluidly coupled to the outlet conduit wherein the grate traps bubbles entrained in the stream of liquid flowing from the containment chamber to the outlet conduit in the containment chamber when the bubbles are greater than or equal to a diameter of a grate inlet;

connecting the bubble trap to a non-pressurized liquid supply;

filling the bubble trap with liquid in a reverse flow direction, from the outlet conduit through the grate inlets of the grate of the bubble trap to remove bubbles from the bubble trap prior to operation of the bubble trap;

directing a stream of liquid through the bubble trap to degas the liquid; and passing a solid in the liquid through the bubble trap.

18. A method for degassing a liquid comprising:
providing a bubble trap comprising
a containment chamber;
an outlet conduit; and
at least one grate disposed between the containment chamber and the outlet conduit, the at least one grate comprising a plurality of grate inlets formed in a grate wall fluidly coupled to the outlet conduit with a plurality of grate conduits such that the containment chamber is fluidly coupled to the outlet conduit wherein the grate traps bubbles entrained in the stream of liquid flowing from the containment chamber to the outlet conduit in the containment chamber when the bubbles are greater than or equal to a diameter of a grate inlet, wherein each of the grate conduits is a single conduit that extends between a respective one of the grate inlets and the outlet conduit;

connecting the bubble trap to a pressurized liquid supply;
evacuating the bubble trap;

filling the bubble trap with liquid in a reverse flow direction, from the outlet conduit through the grate inlets of the grate of the bubble trap to remove bubbles from the bubble trap prior to operation of the bubble trap;

directing a stream of liquid through the bubble trap to degas the liquid; and passing a peptide, protein, hormone, insulin or a solid in the liquid through the bubble trap.

19. The method of claim 18 wherein a peptide is passed in the liquid through the bubble trap.

20. The method of claim 18 wherein a protein is passed in the liquid through the bubble trap.

21. The method of claim 18 wherein a hormone is passed in the liquid through the bubble trap.

22. The method of claim 18 wherein insulin is passed in the liquid through the bubble trap.

23. The method of claim 18 wherein a solid is passed in the liquid through the bubble trap.

24. A method for degassing a liquid comprising:
providing a bubble trap comprising
a containment chamber;
an outlet conduit; and
at least one grate disposed between the containment chamber and the outlet conduit, the at least one grate comprising a plurality of grate inlets formed in a grate wall fluidly coupled to the outlet conduit with a plurality of grate conduits such that the containment chamber is fluidly coupled to the outlet conduit wherein the grate traps bubbles entrained in the stream of liquid flowing from the containment chamber to the outlet conduit in the containment chamber when the bubbles are greater than or equal to a diameter of a grate inlet, wherein each of the grate conduits is a single conduit that extends between a respective one of the grate inlets and the outlet conduit;

connecting the bubble trap to a non-pressurized liquid supply;

filling the bubble trap with liquid in a reverse flow direction, from the outlet conduit through the grate inlets of the grate of the bubble trap to remove bubbles from the bubble trap prior to operation of the bubble trap;

directing a stream of liquid through the bubble trap to degas the liquid; and passing a peptide, protein, hormone, insulin or a solid in the liquid through the bubble trap.

25. The method of claim 24 wherein a peptide is passed in the liquid through the bubble trap.

26. The method of claim 24 wherein a protein is passed in the liquid through the bubble trap.

27. The method of claim 24 wherein a hormone is passed in the liquid through the bubble trap.

28. The method of claim 24 wherein insulin is passed through the bubble trap.

29. The method of claim 24 wherein a solid is passed in the liquid through the bubble trap.

* * * * *

UNITED STATES PATENT AND TRADEMARK OFFICE
CERTIFICATE OF CORRECTION

| | | |
|---|---|---|
| PATENT NO. | : 9,555,197 B2 | Page 1 of 1 |
| APPLICATION NO. | : 14/274128 | |
| DATED | : January 31, 2017 | |
| INVENTOR(S) | : Christoph Huwiler et al. | |

It is certified that error appears in the above-identified patent and that said Letters Patent is hereby corrected as shown below:

In the Specification

Column 5, Line 65:
"Further, the term needle refers to a piercing member (includ-"
Should read:
--Further, the term "needle" refers to a piercing member (includ- --;

Column 10, Line 13:
"the grate inlets 121 are circular or elliptical shape. However,"
Should read:
--the grate inlets 121 are circular or elliptical shaped. However,--; and Column 10, Line 32:
"bubble of a given volume will be larger than for an grate"
Should read:
--bubble of a given volume will be larger than for a grate--.

Signed and Sealed this
Twenty-sixth Day of September, 2017

Joseph Matal
*Performing the Functions and Duties of the
Under Secretary of Commerce for Intellectual Property and
Director of the United States Patent and Trademark Office*